United States Patent [19]

Mori et al.

[11] Patent Number: 4,912,963

[45] Date of Patent: Apr. 3, 1990

[54] METHOD AND AN APPARATUS FOR EVALUATING THE GAS PURIFYING ABILITY OF A GAS PURIFIER

[75] Inventors: Kazuya Mori; Tohru Watanabe; Katsuya Okumura, all of Yokohama, Japan

[73] Assignee: Kabushiki Kaisha Toshiba, Kawasaki, Japan

[21] Appl. No.: 313,529

[22] Filed: Feb. 22, 1989

[30] Foreign Application Priority Data

Feb. 22, 1988 [JP] Japan .................................. 63-39036

[51] Int. Cl.$^4$ ............................................ G01N 15/00
[52] U.S. Cl. ........................................................ 73/38
[58] Field of Search ........................ 73/38, 37, 40, 1 G

[56] References Cited

U.S. PATENT DOCUMENTS 4,056,967 11/1977 Roberts .............................. 73/1 G Primary Examiner—Hezron E. Williams
Assistant Examiner—Joseph W. Roskos
Attorney, Agent, or Firm—Foley & Lardner, Schwartz, Jeffery, Schwaab, Mack, Blumenthal & Evans

[57] ABSTRACT

A method and an apparatus for evaluating the gas purifying ability of a gas purifier are described. The method for evaluating the gas purifying ability comprises the steps of sealing the gas purifier while reducing the inner gas pressure of the gas purifier, releasing a desirable impurity gas shut within a tank at a higher inner gas pressure than the inner gas pressure of the gas purifier, to the sealed gas purifier, and measuring the gas releasing ability of the impurity gas to the gas purifier.

4 Claims, 3 Drawing Sheets

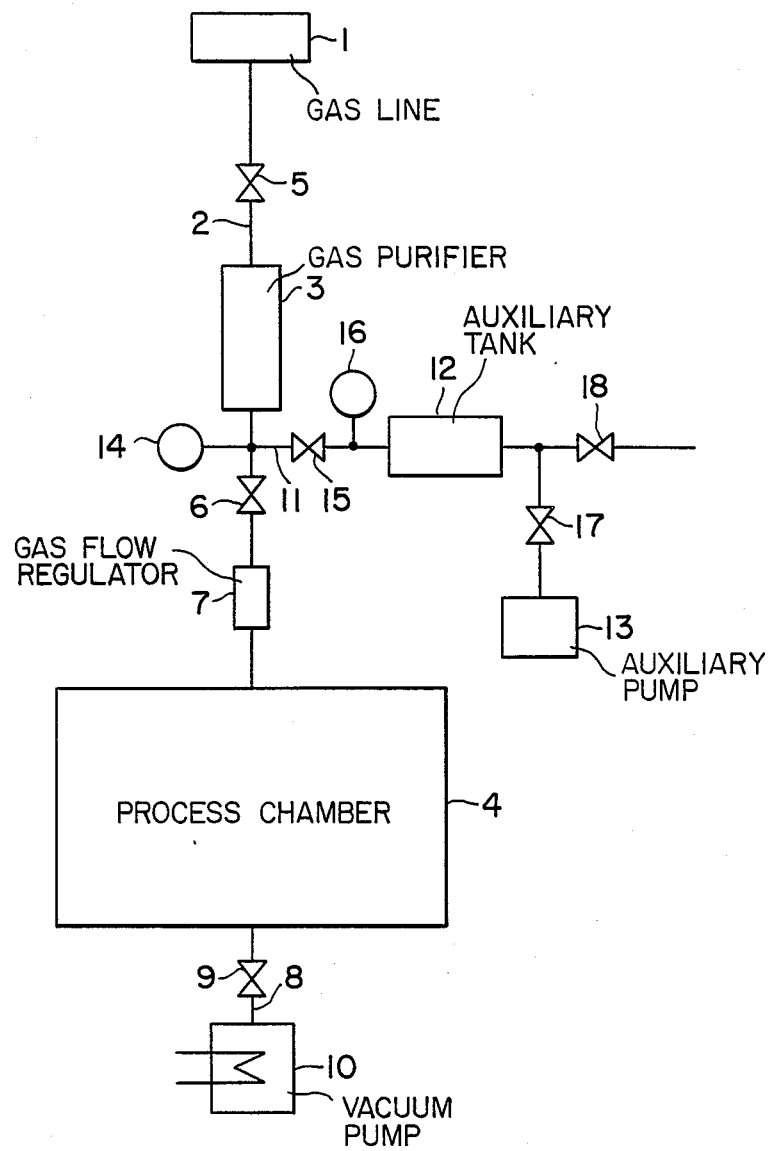
F I G. 1

METHOD AND AN APPARATUS FOR EVALUATING THE GAS PURIFYING ABILITY OF A GAS PURIFIER

FIELD OF THE INVENTION

This invention relates to a method and an apparatus for evaluating the gas purifying ability of a gas purifier of the Getter type that is suitable for making semiconductor devices.

BACKGROUND OF THE INVENTION

Process gases used for making semiconductor devices require higher purity than gases used for general industry, in order to enhance the reliability of semiconductor devices. In particular, the purity of Ar gas generally used in sputtering technology, has a great influence on the reliability of the aluminum wire. Accordingly gas purifiers are generally used for purifying Ar gas. Furthermore, in order to monitor the gas purifying ability of the gas purifiers, a sampling method that extracts Ar gas into a gas container and detects small amounts of impurities by an analysis apparatus such as a gas chromatograph, is traditionally used.

However, as stated above, the sampling method comprising extracting the process gas such as Ar gas into the gas container and detecting impurities such as $N_2$, $O_2$, and $H_2O$ to evaluate the gas purifying ability of the gas purifier require much time. For example, one day is required for extraction and one week for detection, and great cost is entailed. It is therefore difficult to evaluate the gas purifying ability at periodic intervals.

Accordingly, users cannot decide when the gas purifier has to be used, or use the purifier in accordance with times for use indicated by the manufacturers of gas purifiers.

However, gas purifiers which have leaks in their gas lines, will cause the densities of impurities such as $N_2$, $O_2$, and $H_2O$ to increase. If such purifiers are used continually, then the fatal flaws of face leaks and detachment will be caused because of the entry of impure gas into the semiconductor devices. This has been a problem.

SUMMARY OF THE INVENTION

Accordingly, it is an object of the present invention to provide a simple method and apparatus for evaluating the gas purifying ability of a gas purifier of a process gas such as Ar gas, within a short time.

The foregoing object is accomplished by providing a method of evaluating the gas purifying ability of gas purifiers so that the gas purifying ability of the gas purifier can be evaluated, comprising the steps of:

sealing the gas purifier while reducing the inner gas pressure of the gas purifier;

releasing a desired impurity gas contained within a tank at a higher inner gas pressure than the inner gas pressure of the gas purifier to the sealed gas purifier; and measuring the amount of gas release of the impure gas to the gas purifier, and an apparatus for evaluating the gas purifying ability of a gas purifier, comprising:

a sealable gas purifier means for reducing the inner gas pressure therewithin, a tank means for shutting a desired impurity gas at a higher inner gas pressure than the inner gas pressure of the gas purifier, a valve means located the gas purifier means and the tank means for connecting one to the other, a measuring means for measuring the inner gas pressure of the gas purifier.

In the invention, when the gas purifying ability of the gas purifier decreases, the gas releasing ability of the impure gas from the tank having a higher inner gas pressure than the gas purifier, to the gas purifier, also decreases in accordance with decreasing gas purifying ability. Accordingly, by measuring the gas releasing ability, namely by measuring changes in the inner gas pressure of the tank, the gas purifying ability of the gas purifier is evaluated.

BRIEF DESCRIPTION OF THE DRAWINGS

The invention is illustrated diagrammatically in the following drawings wherein:

FIG. 1 is an entire flow diagram of a vacuum apparatus using a carrier gas;

DESCRIPTION OF THE PREFERRED EMBODIMENT

Figure 2:
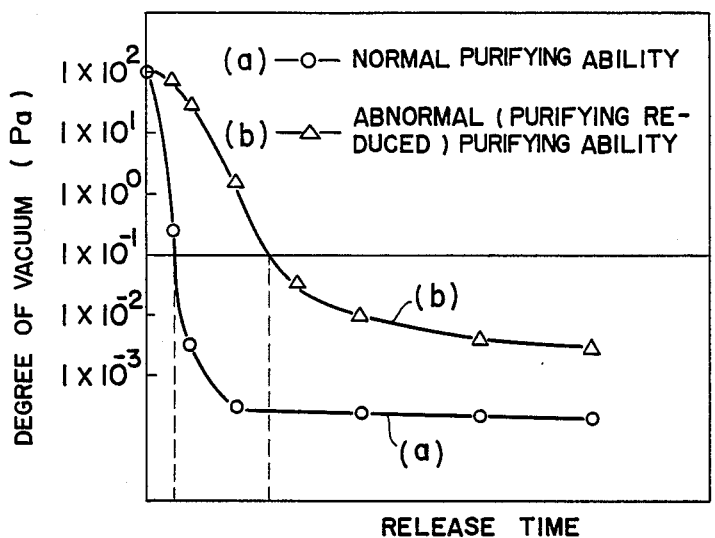
FIG. 2 is a graph showing the relationship between the degree of vacuum of an auxiliary tank and the release time of the auxiliary tank.

Referring to the embodiment of the invention in the drawings. FIG. 1 shows a schematic view of an entire gas use apparatus. In FIG. 1, a process gas, such as Ar gas which is fed from a gas line 1 such as a gas container flows along a main pipe 2, and is purified through a gas purifier 3, and is then introduced into a process chamber 4 such as a sputtering apparatus. A valve 5 is mounted between the gas line 1 of said main pipe 2 and the gas purifier 3, and a valve 6 and a gas flow regulator 7 are mounted between the gas purifier 3 and the process chamber 4 respectively. A release pipe 8 of the process chamber 4 is connected via a valve 9 to a vacuum pump 10. The vacuum pump 10 is operated when the process gas such as Ar gas is introduced into the process chamber, the valves 5, 6 and of the main pipe 2 and the valve 9 of the release pipe 8 are open. Therefore, the gas which is purified through the gas purifier 3 from the gas line 1, is introduced to the process chamber 4, wherein the gas is used for forming a semiconductor member. The used gas is discharged from the process chamber 4.

An auxiliary pipe 11 branches from the main pipe 2 on the outlet side of said gas purifier 3, and an auxiliary tank 12 is mounted on the auxiliary pipe 11. An auxiliary pump 13 is connected to the outlet side of the auxiliary tank 12, and a vacuum gauge 14 such as an ionization vacuum gauge, is mounted at the leading edge of the auxiliary pipe 11, and a valve 15 and a vacuum gauge 16 such as a Pirani gauge are mounted respectively, in series between the leading edge and the auxiliary tank 12. In addition, a valve 17 is mounted between said auxiliary pump 13 and the auxiliary pipe 11, and a valve 18 is mounted at the point farthest from the connection of the auxiliary pipe 11 and the auxiliary pump 13.

The operation for monitoring the purifying ability of said gas purifier 3 is as follows.

First, the valves 5 and 6 are closed (in this case, valve 9 may be either open or closed), and the valves 15 and 17 of the auxiliary pipe 11 are opened, and by operating the auxiliary pump 13 the gas is discharged from the gas purifier 3, the auxiliary tank 12 and the pipe system therebetween. In this case, the degree of vacuum inside them is about $1 \times 10^{-1} \sim 1 \times 10^{-3}$ Pa and is measured by the vacuum gauge 14.

Secondly, the valves 15 and 17 are closed, and the valve 18 is opened from where $N_2$ gas is introduced into the auxiliary tank 12. Therefore, the gas pressure within the auxiliary tank 12 becomes about $1 \sim 1000$ Pa which is higher than that within the gas purifier 3 and is measured by the vacuum gauge 16.

Thirdly, the valve 18 is closed and the $N_2$ gas is shut within the auxiliary tank 12. Then by opening the valve 15 and releasing $N_2$ gas into the gas purifier 3, the released $N_2$ gas is removed (the purifying process) by the gas purifier 3.

In this operation, the $N_2$ gas flows from the auxiliary tank 12 to the gas purifier 3, as a result the gas pressure of the auxiliary tank 12 decreases, as shown in line (a) in FIG. 2. The $N_2$ gas volume (gas releasing ability) which flows from the auxiliary tank 12 to the gas purifier 3 is in accordance with the gas purifying ability of the gas purifier 3. That is to say, when the gas purifying ability of the gas purifier 3 lowers, the gas purifier 3 is not able to remove the $N_2$ gas introduced from the auxiliary tank 12 to the gas purifier 3, and accordingly, the ability to release gas from the tank 12 to the gas purifier 3 decreases as shown by line (b) in FIG. 2. In FIG. 2, the time between the point where line (a) and $1 \times 10^{-1}$ Pa intersect and the point where line (b) and $1 \times 10^{-1}$ Pa intersect, is about one hour.

Figure 3:
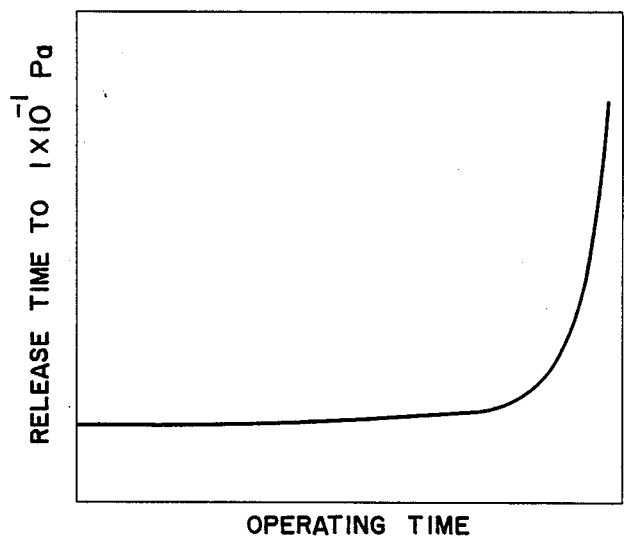
FIG. 3 is a graph showing the relationship between the release time of the auxiliary tank and the working time of a gas purifier.

Also, the results in FIG. 3 are acquired by monitoring the gas purifying ability of the gas purifier 3 for a long time with said monitoring apparatus. That is to say, in FIG. 3 it is understood the gas purifying ability is normal in the initial stage, but then deteriorates with extended use.

Figure 4:
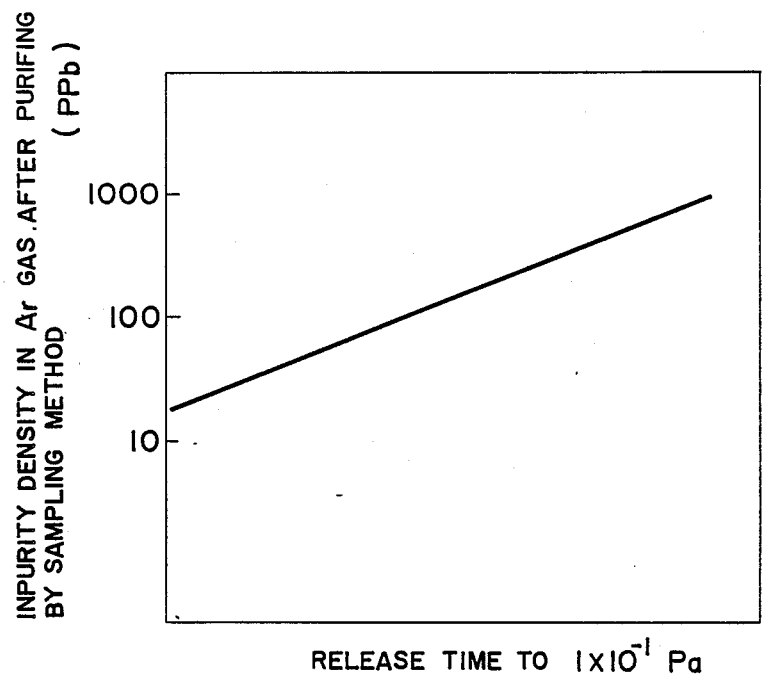
FIG. 4 is a graph showing the relationship between the impurity density and the release time of the auxiliary tank.

FIG. 4 shows the relationship between the time represented logarithmically for releasing until the gas pressure is $1 \times 10^{-1}$ Pa and the gas analysis value obtained by sampling the impurities within the Ar gas which initially includes 10 ppm impurities and is then purified by the gas purifier 3. In FIG. 4, the gas purifying ability has a good relationship with the releasing ability.

In the gas purifier 3, in general by heating an alloy consisting of zirconium (Zr), iron (Fe), and vanadium (V) at about 400° C., impurity gases such as $N_2$, $O_2$, $H_2O$, NO, CO, and $CH_4$ react to be incorporated into the alloy, thus accomplishing the gas purifying process. Accordingly for measuring the gas releasing ability, gases except $N_2$ gas may be introduced into the gas purifier 3.

In above mentioned embodiment, the auxiliary tank 12 and the auxiliary pump 13 is used but alternatively, the process chamber 4 of the sputtering apparatus may serve as a storage tank for the impurity gas, and connected to a pipe for introducing the impurity gas such as $N_2$ gas, so that the impurity gas such as $N_2$ gas is introduced into the process chamber 4 (tank) by the suction operation of the vacuum pump 10. Additionally, when the auxiliary tank 12 is much smaller than the gas purifier 3, for example about 1/1000 to 1/10000, it is possible to shut the air into the auxiliary tank, at atmospheric pressure. In this case, when the valve 15 is opened, the pressure within the gas purifier 3 is about 10 to 1000 Pa.

What is claimed is:

1. A method of evaluating the gas purifying ability of a gas purifier comprising the steps of:
   sealing the gas purifier while reducing the inner gas pressure thereof;
   releasing into the gas purifier a purification evaluation gas, the purification evaluation gas being contained within a tank at a higher inner gas pressure than the inner gas pressure of the gas purifier, the gas flow from the tank to the gas purifier being controlled by a valve located therebetween; and
   measuring the amount of purification evaluation gas released within the gas purifier by measuring the inner gas pressure of the tank.

2. The method of claim 1, wherein the impurity gas is $N_2$.

3. An apparatus for evaluating the gas purifying ability of a gas purifier, comprising: a sealable gas purifier;
   means for reducing the inner gas pressure therein;
   a tank means for providing purification evaluation gas to the gas purifier, the purification evaluation gas being stored within the tank at a higher inner gas pressure than the inner gas pressure of the gas purifier;
   a valve means located between the gas purifier and the tank means for connecting one to the other; and
   a measuring means for measuring the inner gas pressure of the tank means, thereby to measure the amount of gas release of the purification gas by the gas purifier.

4. The apparatus of claim 3, wherein the gas purifier includes an alloy for incorporating the purification evaluation gas.

* * * * *